United States Patent
Kakimoto

[11] Patent Number: 5,211,531
[45] Date of Patent: May 18, 1993

[54] AIR MOTOR

[75] Inventor: Yasuo Kakimoto, Aichi, Japan

[73] Assignee: Ushio Co., Ltd., Nagoya, Japan

[21] Appl. No.: 813,607

[22] Filed: Dec. 26, 1991

[30] Foreign Application Priority Data

Sep. 17, 1991 [JP] Japan .................................. 3-236264

[51] Int. Cl.⁵ ........................ F01D 11/00; F03B 13/04
[52] U.S. Cl. .................................. 415/112; 415/111;
                                                        415/202; 415/904
[58] Field of Search ............... 415/180, 202, 904, 110,
                                                        415/111, 112

[56] References Cited

U.S. PATENT DOCUMENTS

| 3,077,333 | 2/1963 | Gotwald, Jr. et al. | 415/112 |
| 3,123,338 | 3/1964 | Borden | 415/112 |
| 3,304,051 | 2/1967 | Calhoun | 415/904 |
| 3,423,068 | 1/1969 | Hall | 415/904 |
| 3,832,088 | 8/1974 | Cromie | 415/904 |
| 4,040,311 | 8/1977 | Page, Jr. et al. | 415/904 |
| 4,167,062 | 9/1979 | Page, Jr. et al. | 415/904 |
| 5,074,750 | 12/1991 | Kakimoto . | |

Primary Examiner—Thomas E. Denion
Attorney, Agent, or Firm—Sandler Greenblum & Bernstein

[57] ABSTRACT

The invention is directed to a turbine type air motor adapted for use in a hand-piece for dental treatment and includes an air motor body supported by both ends of a turbine shaft with axle-bearings. The air motor includes an air charging passage for introducing compressed air from the rear end, an air discharging passage provided therein in parallel with the air charging passage, and a collet adapted to detachably load a cutting tool. Air flow in the air charging passage is directed to cool one axle-bearing and other air flow in the air discharging passage is directed to cool the other axle-bearing for locally cooling frictional heat generated in both axle-bearings by the high frequency of the air turbine rotation. The collet is devised to easily load the cutting tool by pushing a knock tube provided in the rear end of the hand-piece.

4 Claims, 6 Drawing Sheets

AIR MOTOR

BACKGROUND OF THE INVENTION

1. Field of the Invention

This invention relates to an air motor for using a dental hand-piece and the like, more particularly to an air motor comprising an air turbine supported by axle-bearings mounted on both ends of the air turbine shaft in the motor body of the air motor, wherein compressed air-flow introduced from the end portion of the motor body is supplied through an air charging passage formed within the same body to jet the compressed air into the turbine chamber, thereafter exhaust air discharged from the turbine chamber is further exhausted to outside through an exhaust air discharging passage formed within the same body.

2. Description of the Prior Art

Conventionally such a turbine type air motor is used for a dental hand-piece or another cutting tool of fine work and the like. In case of dental hand-piece, for example, an air motor comprising a collet mounted on one end of hand-piece body to fit a cutting tool with the collet and also an air turbine directly connected with the collet, and compressed air-flow introduced from the rear end of the hand-piece body is then charged into a turbine chamber through an air charging passage formed within the hand-piece body. After the compressed air-flow used in the turbine chamber gives a rotating energy to the air turbine, the discharged air from the turbine chamber is passed so as to be turned back through the exhaust air discharging passage formed within the motor body, wherein the exhaust air is then exhausted to outside from a exhaust port located in a middle position or rear portion of the motor body. The above conventional air turbine, which is connected with the collet, is then rotated in a state so that the both ends of turbine shaft are supported by two pieces of the axle-bearings and thus the rotation frequency of air turbine reaches approximately 200,000 to 300,000 r.p.m. (revolutions per minute).

As a disadvantage of such conventional air turbine, however, due to this high frequency for the turbine rotation, the axle-bearings of supporting the turbine shaft inevitably generate frictional heat, consequently the life of axle-bearing is rapidly shortened if no heat radiation is provided to the bearing portion.

SUMMARY OF THE INVENTION

Accordingly, it is an object of the present invention to provide a cooling means for axle-bearings to support the main shaft of the air turbine of the above air motor, and then provide the prolongation of the axle-bearing life.

Accordingly, as a technical means provided by the present invention to solve the above disadvantages in the conventional air motor, the present invention provides an air motor comprising an air turbine encased in the air motor body by supporting both ends of the turbine shaft with a plurality of axle-bearings; a turbine chamber having a compressed air charging passage formed within the motor body to introduce compressed air from the end portion of the air motor body to jet into the turbine chamber, and also having an exhaust air discharging passage formed within the same body to discharge exhaust air from the turbine chamber to exhaust outside from the motor body, characterized in that the above compressed air charging passage is made to fluidly communicate to one axle-bearing for supporting one end of the air turbine shaft and also the above exhaust air discharging passage is made to fluidly communicate to the other axle-bearing for supporting the other end of the turbine shaft.

According to the technical means of the present invention, the compressed air to be charged into the turbine chamber through the compressed air charging passage comes into contact with one axle-bearing for supporting one end of the turbine shaft, wherein the axle-bearing is cooled by the compressed air charging flow on the way to the turbine chamber. Besides, the exhaust air discharged from the turbine chamber through the exhaust air discharging passage also comes into contact with the other axle-bearing of supporting the other end of the turbine shaft wherein the other axle-bearing is cooled by the exhaust air on the way to the outside from the motor body.

Accordingly, the present invention is advantageous in that since the both axle-bearings for supporting the turbine shaft should be cooled by the air flow to be charged into the turbine chamber through the compressed air charging passage, and also the other air flow to be discharged from the turbine chamber through the exhaust air discharging passage, the frictional heat generated by the high frequency of the turbine shaft rotation with respect to both side axle-bearings can be cooled by both side air flows without any size-enlargement of the motor or making complex the motor structure.

BRIEF DESCRIPTION OF THE DRAWINGS

FIG. 1B illustrates an enlarged detail of a portion B, of FIG. 1A, FIG. 2(a) to FIG. 2(e), FIG. 2(g) and FIG. 2(h) illustrate each section view defined from a—a line to e—e line, g—g line and h—h line in FIG. 1A.

DETAILED DESCRIPTION OF THE INVENTION

Referring now in detail to a preferred embodiment of the present invention based on the drawings hereinafter:

FIG. 1 to FIG. 6 illustrate a dental hand-piece, the hand-piece body 1 comprising of a turbine type air motor A encased in a turbine chamber 3 of the air motor A provided in the interior of the front portion of the hand-piece body 1, the turbine chamber 3 is charged by a compressed air introduced from an air hose 23 fixed to the rear end of the hand-piece body 1; a compressed air charging passage 8 positioned between the turbine chamber 3 and the air hose 23 in the hand-piece body 1 to charge the compressed air into the turbine chamber 3; and a exhaust air discharging passage 9 provided parallel to the compressed air charging passage 8 in the same body 1 to exhaust a discharged air to outside from the turbine chamber 3 of the air motor A through an exhaust air outlet 26 provided in the rear end of the same body 1.

In the drawings, it illustrates that the referential numeral 1 is a hand-piece body, the numeral 2 is a turbine, the numeral 3 is a turbine chamber, the numeral 4 is a turbine shaft, the numerals 5 and 6 are a plurality of axle-bearings to support the turbine shaft, the numeral 7 is a collet, the numeral 8 is a compressed air charging passage, and the numeral 9 is a exhaust air discharging passage.

As an aspect, the hand-piece body 1 has an almost pencil shape with a hollow cylinder portion therein, the hand-piece body 1 comprising of two members such as a front cylindrical casing 1a and a rear cylindrical casing 1b, the two members are coupled as a screw coupling each other at their central positions, and a turbine casing 11 inserted by a push fit into the front end of the front cylindrical casing 1a.

The turbine casing 11 is shaped as a cylinder, the interior of the turbine casing 11 forms a turbine chamber 3 to house the turbine rotor 2, and the turbine casing 11 has a stepped portion 11a as a collar of an axle-bearing 5 therein at the end face of the end portion thereof, and the turbine casing 11 is housed by a push-fit into the front cylindrical casing 1a through the rear opening of the front cylindrical casing 1a toward the interior end of the same 1a after mounting a packing such as an O-ring in advance on the periphery edge of the stepped portion 11a to seal the joint portion between the interior end and stepped portion 11a of the turbine casing 11.

Figure 4:
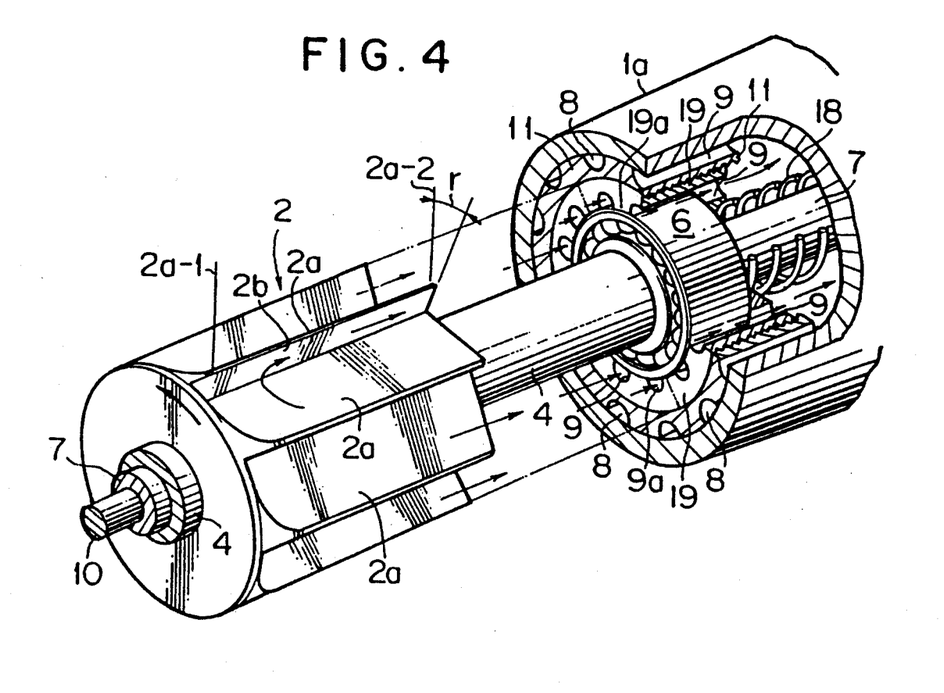
FIG. 4 illustrates a partially broken perspective view for showing an axle-bearing portion provided in the rear end portion of the hand-piece.

In FIG. 4, referring to the structure of the turbine rotor 2 to be housed into the turbine chamber 3 of the turbine casing 11, the turbine rotor 2 comprising of a turbine rotor 2 formed as an octagonal gear shape in the sectional view with eight pieces of blade wings 2a thereof, and a shaft 4 of supporting the turbine rotor 2 to be inserted into and passed through the bored axis center of the rotor 2 to receive the insertion of the shaft 4 wherein the turbine rotor 2 is rotatably supported by the shaft 4 within the turbine chamber 3. Regarding the structure of the shaft 4, the core portion of the shaft 4 is formed as a hollowed cylinder.

The both ends of the shaft 4 with the turbine rotor 2, that is, the front and rear ends of the turbine rotor 2 with the shaft 4 are supported by both axle-bearings 5 and 6, the axle-bearing 5 of the front end side is mounted within the stepped bearing collar portion 11a of the turbine casing 11 and the axle-bearing 6 of the rear end side is mounted within a rear bearing collar 19 in FIG. 4. The inner circumference 19a of the rear bearing collar 19 is to receive the axle-bearing 6 and the outer circumference of the collar 19 is thread-cut to engage with the rear opening of the rear cylindrical portion 1b of the turbine casing 11 wherein the turbine rotor 2 is rotatably supported within the turbine chamber 3.

Figure 2A:
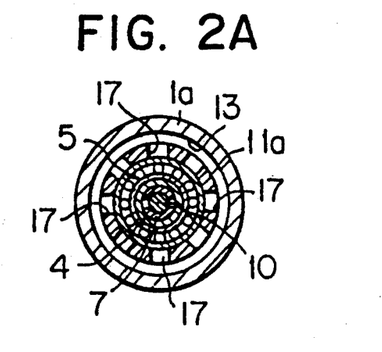
Figure 2B:
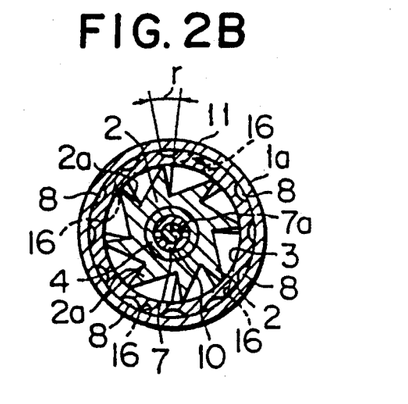

Regarding the shape of each blade wings 2a of the turbine rotor 2, as illustrated in FIG. 2(b) and FIG. 4, the angle of a pressure receiving surface 2b of a blade end 2a-1 (FIG. 4) provides a leading-angle (r) so as to be more twisted with an angle such as approximately 5 degree than the angle of the pressure receiving surface 2b of the blade end 2a-1, which is twisted toward the contrary direction of the rotation direction of the rotor 2. According to the leading-angle (r), the turbine rotor 2 can be possible to efficiently convert the jet-energy of compressed air into a rotation energy.

Regarding the detailed structure of the turbine casing 11 to be encased within the front cylindrical portion 1a in FIG. 4, the turbine casing 11 provides two kind concave grooves longitudinally surrounding on the outer circumference of the turbine casing 11 such as one group is long grooves fully covering the total length of the turbine casing 11 and the other group is short grooves provided only in the front half portion of the turbine casing 11, the long type grooves are referred to as a plurality of air charging grooves 14 and the short type grooves are a plurality of air charging grooves 15 and both type grooves 14 and 15 are formed side by side along the longitudinal direction of the turbine casing 11 in parallel each other on the outer circumference thereof.

Figure 3:
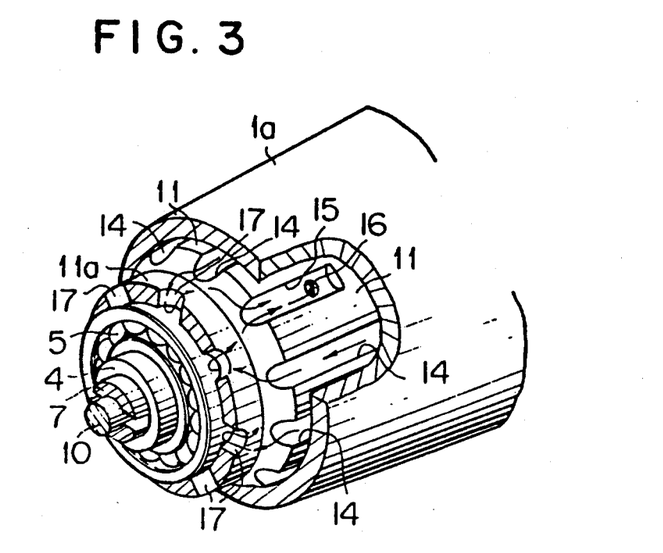
FIG. 3 illustrates a partially broken perspective view for showing an axle-bearing portion provided in the front end portion of the hand-piece.

Regarding the air charging groove 15, i.e., the short type groove, each air charging groove 15 provides a jetting nozzle 16 respectively to jet the compressed air into the turbine chamber 3, this jetting nozzle 16 is bored at the dead end of the short groove 15 with a inclined angle toward the interior of the turbine chamber 3 as illustrated in FIG. 3.

Figure 1A:
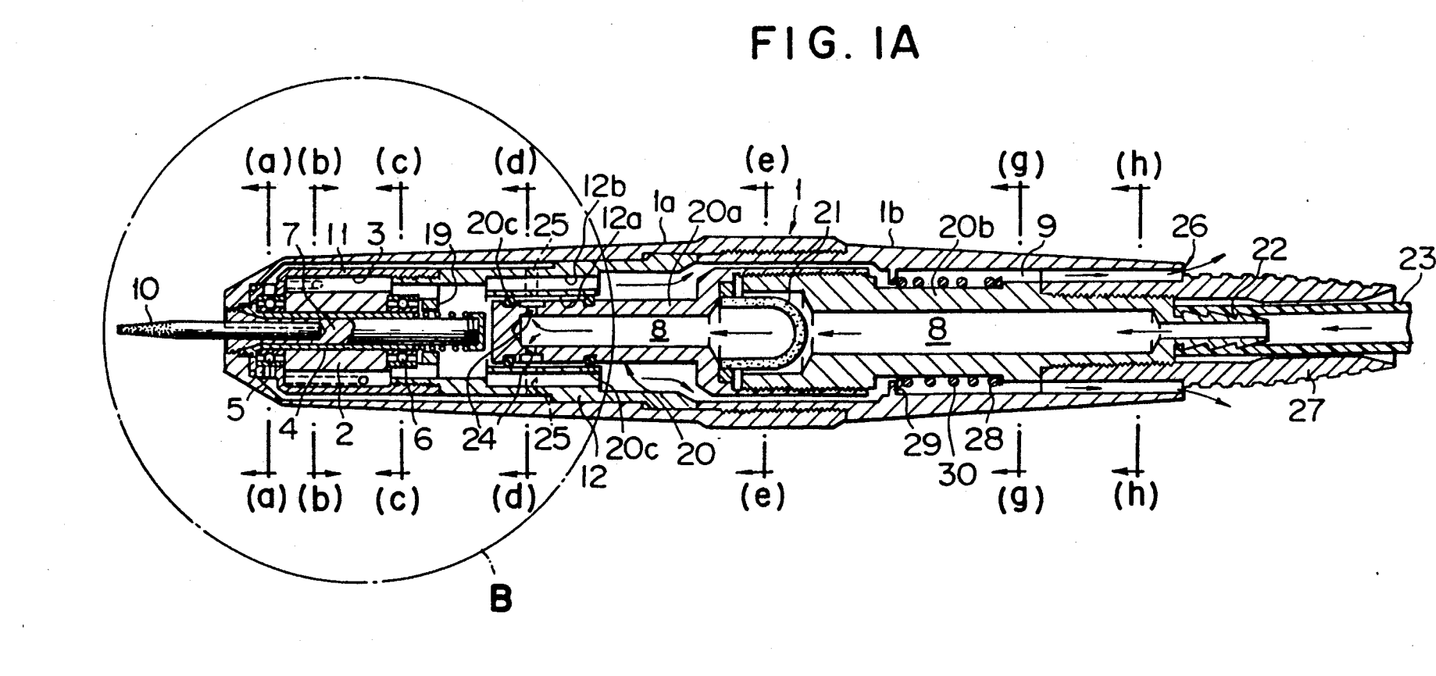
FIG. 1A illustrates a longitudinal sectional view for showing a hand-piece having an air motor practiced in the present invention.
Figure 1B:
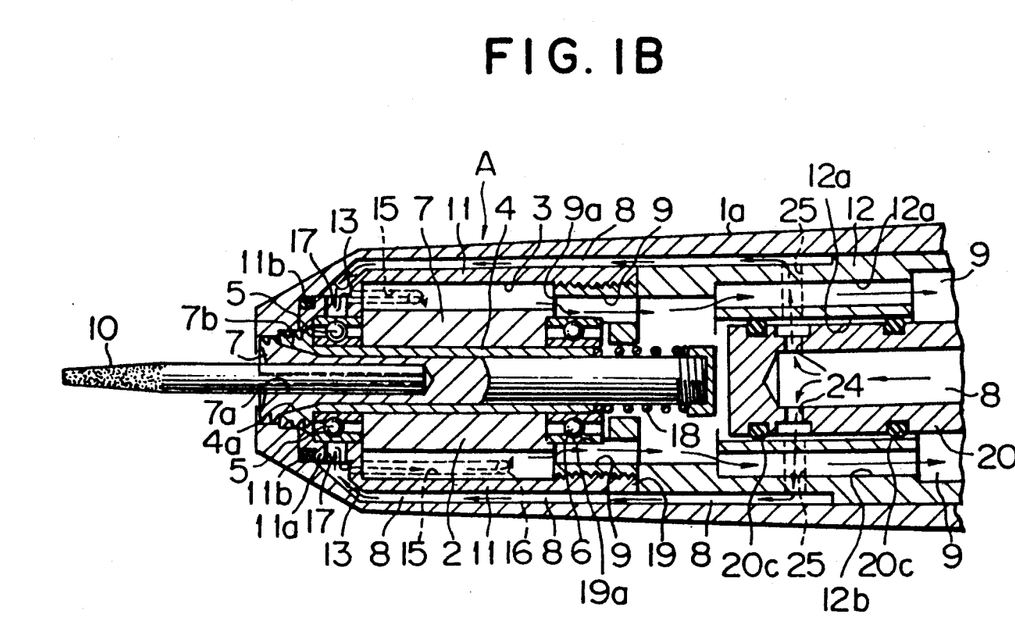

According to the plurality of the jetting nozzles 16, a plurality of a compressed air charging passages 8 are formed from the rear end of the turbine casing 11 through the air charging grooves 14, once the air flow reaches at a dead end space 13 formed in the interior of the front end of the front cylindrical portion 1a (FIG. 1), and made a U-turn toward the air charging grooves 15 to be jetted into the turbine chamber 3 through the jetting nozzles 16. (FIG. 3)

Thus, the compressed air flow passed through the compressed air charging passages 8 (i.e., comprising of the grooves 14 and 15) and jetted into the turbine chamber 3 through four pieces of the jetting nozzles 16 will push the blade wings 2a of the turbine rotor 2, and made to flow toward the rear end of the turbine chamber 3 while giving the rotation energy toward a predetermined direction to the turbine rotor 2, wherein the air flow is finally discharged into an air discharging passage 9 from an air discharging port 9a provided in the rear end of the turbine chamber 3.

The following is a significant aspect of the present invention relating to the cooling system of the axle-bearings.

Due to the above turbine rotor 2 forced to rotate at more than 200,000 r.p.m. by the rotation energy given by the compressed air flow and a certain amount of the frictional heat generation and condensation in the both axle-bearings 5 and 6 to support the high frequency of turbine rotor rotation, the present invention provides to prevent the excessive heat generation and condensation of the both axle-bearings 5 and 6 by utilizing the air flow in the air charging passages 8 and the air discharging passages 9 and then cooling both axle-bearings 5 and 6.

Regarding the cooling mechanism of the front axle-bearings 5, as illustrated in FIG. 3, it comprises that a plurality of air cooling holes 17 are bored on the circumferential surface of the stepped collar portion 11a of the turbine casing 11 so as to expose the circumferential surface of the front axle-bearing 5 from the air cooling holes 17 and to cool the front axle-bearing 5 by a partial amount of the air flow made a U-turn from the air charging passages 8 to the air discharging passages 9 within the dead end space 13.

Regarding the cooling mechanism of the rear axle-bearing 6, as illustrated in FIG. 1 and FIG. 4, it comprises that a plurality of air cooling grooves are longitudinally provided on the inner circumferential surface 19a of the bearing collar 19 to cool the outer circumferential surface of the axle-bearing 6 by using a discharging air flow from the turbine chamber 3.

Figure 5:
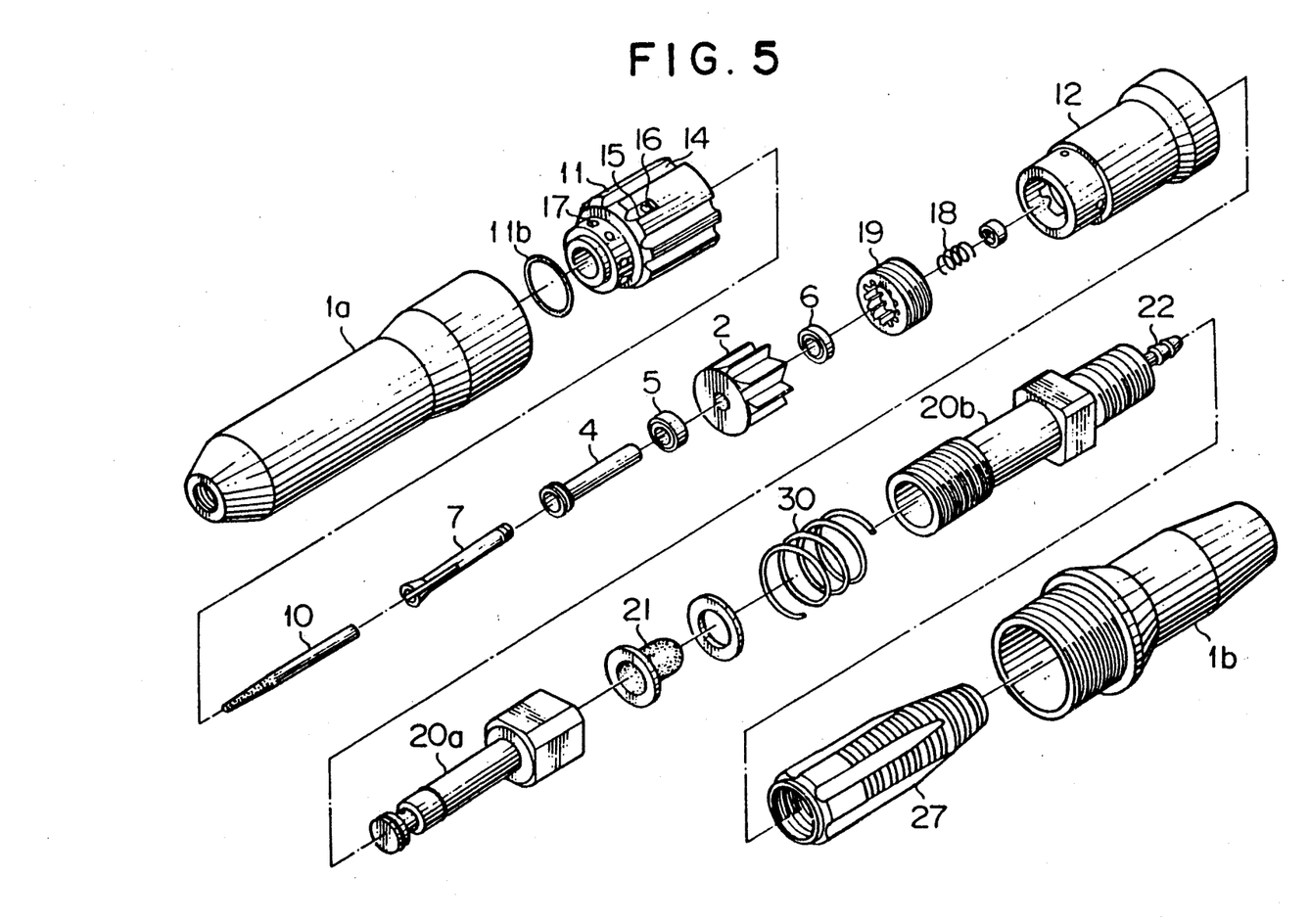
FIG. 5 illustrates a perspective view of each part dismantled from the hand-piece.

The configuration between the rear axle-bearing 6 and the bearing collar 19 with the plurality of air cooling grooves is schematically illustrated in FIG. 5. The bearing collar 19 acts as the blind flange of the turbine casing 11, simultaneously acts as the air cooling of the axle-bearing 6 as well as acts as the first inlet of the air discharging passage 9.

According to this cooling means employed by the present invention, it is advantageous in that it can provide a reasonable and effective cooling upon the axle-bearings of the turbine rotor since it utilizes the high speed air flow of charging and discharging air required to drive the hand-piece, and further provides a compact sized air motor to be used for a hand-piece with a simplified structure.

Referring now in detail to a collect 7 which detachably holds a cutting tool 10, and its mechanism and operation.

As illustrated in FIG. 1 and FIG. 5, it is clear that the collet 7 is a so-called slitting attachment, the collect 7 comprising a slit 7a to receive the insertion of the cutting tool 10 along the axis of the front end portion, and a inverted taper surface 7b provided in the front end of the slit 7a.

The stem portion of the collet 7 is then slidably inserted into the hollowed cylindrical portion of the rotation shaft 4 and a pulling type coil spring 18 interconnects between the rear end of the stem portion of the collet 7 and the rear end of the rotation shaft 4, wherein the stem portion of the collet 7 is constantly urged rearward by the pulling type coil spring 18 so as to slidably move the front face of the inverted taper surface 7b of the collet 7 to come out from or come into a receiving mouth 4a formed in the inner circumferential surface of the front end opening of the rotation shaft 4.

In this aspect, regarding the loading operation of the cutting tool 10 on the collet 7, the inverted taper surface 7b of the collet 7 is throttled within the receiving mouth 4a of the shaft 4 having the same taper angle with the inverted taper surface 7b of the collet 7 to tightly hold the cutting tool 10 in the slit 7a of the collet 7. Regarding the unloading of the cutting cool 10 from the collet 7, the cutting tool 10 is easily unloaded after releasing the throttle acted between the inverted taper surface 7b and the same taper surface of the receiving mouth 4a by pulling the front end of the collet 7 against the urge of the spring coil 18.

A sleeve 12 and a piston body 20 are combined together and housed into the rear half portion of the turbine casing 11. The sleeve 12 is a cylindrical body to be inserted into the inner circumferential surface of the front cylindrical portion 1a and the diameter of the inner cylinder 12a of the sleeve 12 is reasonably smaller than the outer diameter of the sleeve 12. The front end of the sleeve 12 longitudinally provides a plurality of air discharging holes 12b in parallel with the axis of the inner cylinder 12a of the sleeve 12, and the stem portion of the piston body 20 with O-rings 20c is slidably inserted into the inner cylinder 12a of the sleeve 12. The piston body 20 is also a cylindrical body and comprises the front half portion 20a of the piston body 20 and the rear half portion 20b of the piston body 20, both portions 20a and 20b of the piston body 20 being coupled by screw at their middle position. Further, the rear half portion 20b of the piston body 20 provides a hose coupler 22 so as to project further rearward from the rear end of the rear half portion 2b to couple an air charging hose 23 with the hose coupler 22, and the longitudinal inner cylinder portion of the rear half portion 2b of the piston body 20 to be used as an air charging passage 8 to fluidly communicate with the air motor A.

The rear end of the front half portion 20a is formed as a different size socket with a inner thread to couple by screwing to the outer thread of the rear half portion 20b as schematically illustrated in FIG. 5 and FIG. 1.

In FIG. 1, the opening of the front end of the rear half portion 20b is partially larger than the the air charging passage 8 of the rear half portion 20b to receive an air filter 21 between the inner flange portion of the different size socket of the front half portion 20a and the enlarged opening of the rear half portion 20b to filtrate the compressed air flow fed through the air charging passage 8.

Figure 2D:
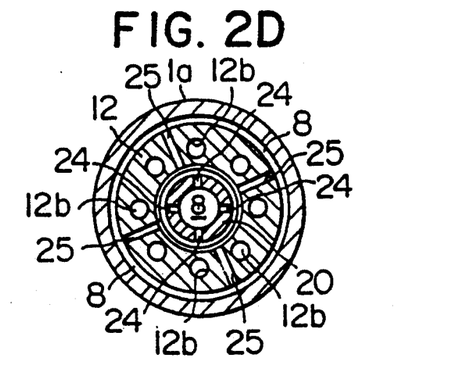

In FIG. 1 and FIG. 2(d), a plurality of vent holes 24 are radially bored around the front end of the front half portion 20a between both O-rings 20c to deliver the compressed air flow fed through the air charging passage 8 to a next receiver, i.e., the sleeve 12. A plurality of other vent holes 25 are radially bored around the front end of the sleeve 12 to receive the air from the vent holes 24 of the front half portion 20a to further deliver the air into the air charging passage 8 provided in the outer circumferential surface of the turbine casing 11.

An air discharging mechanism of the hand-piece body 1 is now described.

Figure 2E:
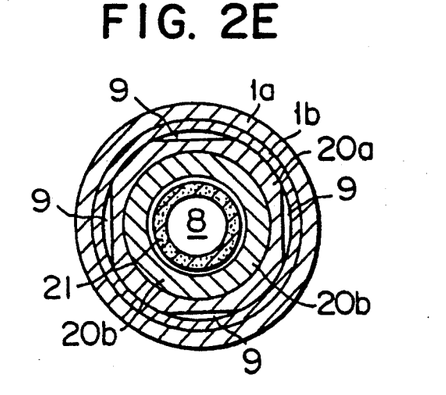
Figure 2G:
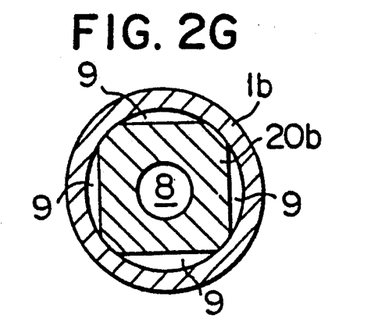
Figure 2H:
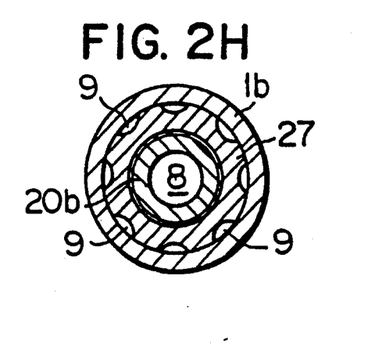

As schematically illustrated in the sectional views of FIGS. 2(c), (e), (g) and (h), the air discharging passages 9 are variously formed in each section so that they are shaped as a plurality of grooves to contact the axle-bearing in FIG. 2(c) or to contact a rear casing 1b in FIG. 2(h), or shaped as a plurality of half circular spaces in FIGS. 2(e) and (g), as well as the air charging passages 8 are also variously formed alternately with the air discharging passages 9 in each section as described above.

The air discharging passages 9 comprising a plural number of desired spaces having a half circle shape provided between the outer circumferential surface of the piston body 20 and the inner circumferential surface of the sleeve 12, and the inner circumferential surface of the rear casing 1b, and the plural number of desired spaces comprises the air discharging passage 9 to communicate between the air discharging passage 9 provided in the bearing collar 19 of the rear end opening of the turbine casing 11 and an air exhausting ports 26 provided at the most rear end of the rear casing 1b.

In this construction, discharged air from the the turbine chamber 3 is discharged rearward through the air cooling grooves of the bearing collar 19, then passed through the plurality of air discharging holes 12b provided in the front end of the sleeve 12 and further flows along the outer peripheral surface of the connecting portion of the piston body 20 and finally exhausted outside from the air exhausting port 26 provided between a knock tube 27 engaged by a screw with the rear portion of the piston body 20 and the rear casing 1b.

A coil spring 30 is disposed between a stepped portion 28 provided in the rear portion of the piston body 20 and a flange portion 29 provided in the inner circumference of the rear casing 1b, according to this coil spring 30, the piston body 20 is constantly urged backward so as to contact a stepped portion 31 of the connected portion with the flange portion 29 to be positioned at the most rearward position. Further, when the piston body 20 is in the most rearward position, it is made to maintain a certain gap between the end of the piston body 20 and the rear end of the collet 7.

Figure 6:
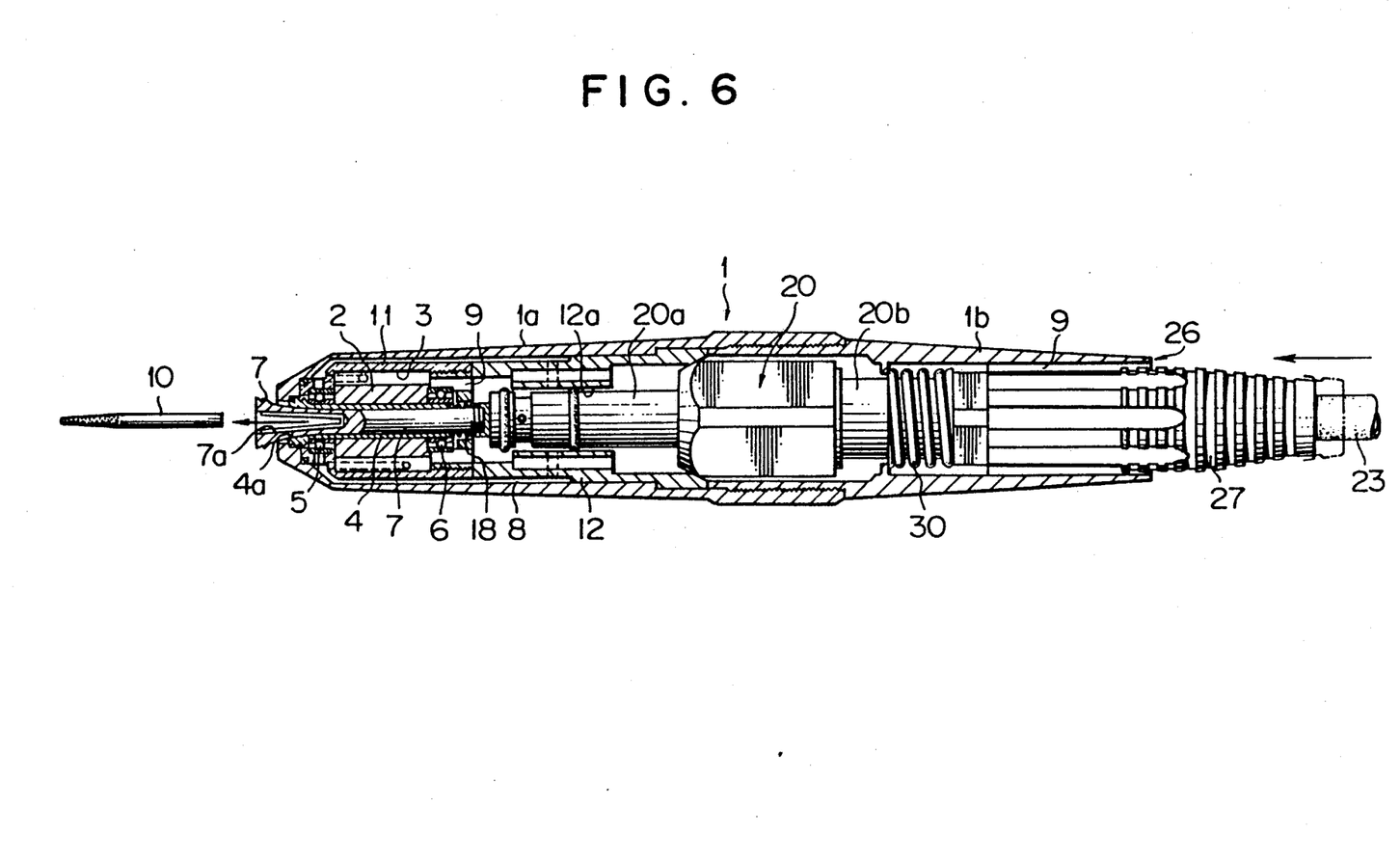
FIG. 6 illustrates a longitudinal sectional view for showing the hand-piece in state of that a piston body is extruded.

In this aspect, the piston body 20, which is housed in the handpiece body 1 as previously described, is slidably held within the sleeve 12 by inserting the front end of the piston body 20 into the sleeve 12 and by pushing the knock tube 27 frontward against the urging of the coil spring 30, the head of the piston body 20 will knock the rear end of the stem of the collet 7 which is constantly urged rearward by the coil spring 18 and then the cutting tool 10, which is held in the slit 7a, is pushed out to be unloaded from the collet 7, (FIG. 6). This is another advantage of the present invention to provide an easy unloading mechanism of the cutting tool.

Because, conventionally, when loading or unloading the so-called cutting tool on or from the collet of a hand-piece, it is manually loaded or unloaded by pushing or pulling it from the collet, however, according to the development of various type tools, the size of the tool becomes smaller and then it becomes not only difficult but also dangerous to manually load or unload such a miniaturized cutting tool by hand.

In contrast the collet 7 of the hand-piece of the present invention is capable of detachably loading any miniaturized cutting tool 10 on the collet 7 by only pushing the knock tube 27, and needless to say, this easy loading mechanism is usable for any tool other than for dental use in a fine machining field.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. An air motor including a turbine housed within an air motor body by supporting both ends of a turbine shaft with axle-bearings, an air charging passage longitudinally provided within the air motor body to introduce compressed air from the rear end of the air motor body for jetting the compressed air into a turbine chamber, and an air discharging passage provided therein in parallel with the air charging passage to discharge exhaust air from the turbine chamber, said air motor comprising:

one axle-bearing for supporting one end of the turbine shaft, the one axle-bearing being positioned to contact charging air flowing in the air charging passage;

an other axle-bearing for supporting the other end of the turbine shaft, the other axle-bearing being positioned to contact discharging air flowing in the air discharging passage;

wherein a turbine casing having the turbine chamber comprises one end being formed as a stepped portion having a smaller diameter than that of the turbine casing, and the other end thereof being formed as an opening, the one axle-bearing being fitted into the stepped portion to make the axle-bearing contact the charging air flowing in the air charging passage, and the other axle-bearing being fitted into a bearing collar which is screwed in the turbine casing to make the other axle-bearing contact the discharging air flowing in the air discharging passage; and wherein a plurality of air cooling holes are radially bored around an outer circumferential surface of the stepped portion of the turbine casing to expose an outer circumferential surface of the one axle-bearing to the air flow in the air charging passage through the plurality of air cooling holes, and a plurality of air cooling grooves being radially provided along an axis of the bearing collar, the air cooling grooves being provided around an inner circumferential surface of the bearing collar which comprises a first inlet of the air discharging passage, and the plurality of air cooling grooves exposing an outer circumferential surface of the other axle-bearing to the air flow in the air discharging passage.

2. An air motor according to claim 1, comprising a turbine rotor having a plurality of blade wings, wherein each blade wing of the turbine rotor is provided with a predetermined angle in its front end and rear end, respectively.

3. An air motor including a turbine housed within an air motor body by supporting both ends of a turbine shaft with axle-bearings, an air charging passage longitudinally provided within the air motor body to introduce compressed air from the rear end of the air motor body for jetting the compressed air into a turbine chamber, and an air discharging passage provided therein in parallel with the air charging passage to discharge exhaust air from the turbine chamber, said air motor comprising:

one axle-bearing for supporting one end of the turbine shaft, the one axle-bearing being positioned to contact charging air flowing in the air charging passage;

an other axle-bearing for supporting the other end of the turbine shaft, the other axle-bearing being positioned to contact discharging air flowing in the air discharging passage; and wherein the turbine shaft is formed as a cylinder shaft having a dead end at a rear end and a bugle shaped tapered-opening at a front end for slidably fitting a stem of a collet, the collet detachably fitting a cutting tool within a slit of the collet, the rear end of the cylinder shaft being provided to project from the rear end of a bearing collar, a coil spring being mounted on the rear end of the cylinder shaft to constantly urge the cylinder shaft rearwardly, a knock tube being provided within the rear end portion of the air motor body, the knock tube being connected with a piston body, the piston body with the knock tube being slidably provided within the air motor body to oppose the front end of the piston body with the rear end of the collet being urged rearwardly by the coil spring, whereby the collet detachably fits a cutting tool by pushing the knock tube with the piston body.

4. An air motor according to claim 3, wherein a turbine casing having the turbine chamber comprises one end being formed as a stepped portion having a smaller diameter than that of the turbine casing, and the other end thereof being formed as an opening, one axle-bearing being fitted into the stepped portion to make the axle-bearing contact the charging air flowing in the air charging passage, and the other axle-bearing being fitted into a bearing collar which is screwed in the turbine casing to make the other axle-bearing contact the discharging air flowing in the air discharging passage.

* * * * *